United States Patent [19]

Brown et al.

[11] Patent Number: 4,466,970

[45] Date of Patent: Aug. 21, 1984

[54] DIOXOCYCLOBUTENE COMPOUNDS

[75] Inventors: Thomas H. Brown, Tewin; Rodney C. Young, Hertford, both of England

[73] Assignee: Smith Kline & French Laboratories Limited, Welwyn Garden City, England

[21] Appl. No.: 535,467

[22] Filed: Sep. 26, 1983

[30] Foreign Application Priority Data

Oct. 2, 1982 [GB] United Kingdom ................. 8228207
Nov. 13, 1982 [GB] United Kingdom ................. 8232468

[51] Int. Cl.$^3$ .................. A61K 31/44; A61K 41/445; C07D 401/12
[52] U.S. Cl. ..................................... 424/263; 424/267; 546/194; 546/281; 546/275; 546/193; 546/213
[58] Field of Search ............... 546/281, 275, 194, 213; 424/267, 263

[56] References Cited

U.S. PATENT DOCUMENTS 4,062,863 12/1977 Ganellin et al. ..................... 424/263
4,390,701 6/1983 Algieri et al. ........................ 424/267
4,395,553 7/1983 Algieri et al. ........................ 424/267

OTHER PUBLICATIONS

*Derwent Abstract* 02282J (abstract of Belgian 893,236, published Nov. 18, 1982).

*Primary Examiner*—Robert T. Bond
*Attorney, Agent, or Firm*—Joan S. Keps; Richard D. Foggio; Alan D. Lourie

[57] ABSTRACT

1-(4-Dialkylaminomethylpyrid-2-yloxypropylamino)-2-aminocyclobut-1-ene-3,4-dione compounds having histamine $H_2$-antagonist activity are disclosed.

8 Claims, No Drawings

DIOXOCYCLOBUTENE COMPOUNDS

This invention relates to dioxocyclobutene derivatives, pharmaceutical compositions containing them and their use as histamine $H_2$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427 (1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine $H_1$- and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

Accordingly the present invention provides a compound of the formula (I):

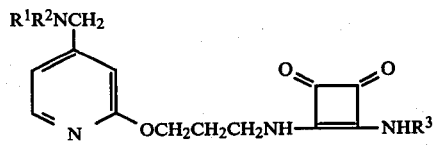

or a pharmaceutically acceptable salt thereof, wherein
$R^1$ and $R^2$ are independently hydrogen or $C_{1-6}$ alkyl, or $R^1R^2N$ represents 2,2,2-trifluoroethylamino; or
$R^1$ and $R^2$ form a $-(CH_2)_n-$ linkage, wherein n is 4-6, so that together with the nitrogen atom to which they are attached they form a 5-7 membered ring; and
$R^3$ is hydrogen or $C_{1-6}$ alkyl.

Suitably $R^1$ is methyl, ethyl, n-propyl or isopropyl. Suitably $R^2$ is hydrogen, methyl, ethyl or n-propyl. In one suitable aspect $R^1R^2N-$ represents dimethylamino. In a further suitable aspect $R^1R^2N$ represents 2,2,2-trifluoroethylamino. Preferably $R^1R^2NCH_2-$ represents pyrrolidinomethyl, piperidinomethyl or hexahydroazepinomethyl. Piperidinomethyl is particularly favoured.

Suitably $R^3$ is hydrogen or $C_{1-6}$alkyl such as methyl, ethyl, n-propyl or isopropyl. Suitably $R^3$ is hydrogen or methyl.

In a favoured aspect $R^3NH-$ represents amino.

The activity of the compounds of formula (I) as histamine $H_2$-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. These are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

The measurement of inhibition of histamine-stimulated secretion of gastric acid from the lumen-perfused stomachs of rats anaesthetised with urethane, and the measurement of inhibition of histamine-induced tachycardia in the isolated guinea pig right atrium, are detailed in our European Patent Application Publication No. 49173.

To illustrate the level of activity of the compounds of the present invention we have determined that the products of the Examples have $ED_{50}$ values in the lumen-perfused rat test of less than one micromol $kg^{-1}$ i.v. and $pA_2$ values in the guinea pig atrium test of more than six.

The compounds of this invention are significantly more active and have a longer duration of action than the related compounds wherein the $R^1R^2NCH_2-$ group is substituted at the 6-position of the pyridyl group.

In addition, we have found that the compound of Example 1 shows a significant increase in duration of action over that of cimetidine after intravenous administration in the Heidenhain pouch dog, when dose levels had been adjusted to produce similar peak responses.

In order to use compounds of formula (I) or pharmaceutically acceptable salts thereof for medical purposes, they are normally formulated in accordance with standard pharmaceutical practice as pharmaceutical compositions.

This invention further provides pharmaceutical compositions comprising a compound of formula (I) above or a pharmaceutically acceptable salt thereof together with a pharmaceutically acceptable carrier.

Compounds of formula (I) and their pharmaceutically acceptable salts may be administered orally, parenterally, cutaneously or rectally.

Compounds of formula (I) and their pharmaceutically acceptable salts which are active when given orally can be formulated as syrups, tablets, capsules and lozenges. A syrup formulation will generally consist of a suspension or solution of the compound or salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound or salt in a sterile aqueous carrier or parenterally acceptable oil.

Typical compositions for administration to the skin include lotions and creams in which the compound of formula (I) or salt thereof is contained in a liquid vehicle.

A typical suppository formulation comprises a compound of formula (I) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains preferably from 1.5 to 25 mg) of a compound of formula (1) or a pharmaceutically acceptable salt thereof calculated as the free base.

The invention also provides a method of blocking histamine $H_2$ receptors which comprises administering to an animal an effective amount to block said receptors of a compound of formula (1) or a pharmaceutically acceptable acid-addition salt thereof.

The compounds of the invention will normally be administered to a subject for the treatment of peptic ulcers and other conditions caused or exacerbated by gastric acidity in the same general manner as that employed for known histamine $H_2$-antagonists, due allowance being made in terms of dose levels for the potency of the compound of the present invention relative to known histamine $H_2$-antagonists. The daily dosage regimen for an adult patient is an oral dose of between 15 mg and 1500 mg, and preferably between 20 mg and 250 mg, or an intravenous, subcutaneous, or intramuscular dose of between 1.5 mg and 150 mg, and preferably between 5 mg and 20 mg, of compound of formula (I) or a pharmaceutically acceptable salt thereof calculated as the free base, the composition being administered 1 to 6 times per day.

The compounds of this invention show no overt signs of toxicity at pertinent dosage levels.

The compounds of the formula (I) and pharmaceutically acceptable acid addition salts thereof may be prepared by a process which comprises:

(a) the reaction of a compound of the formula (II) with a compound of the formula (III):

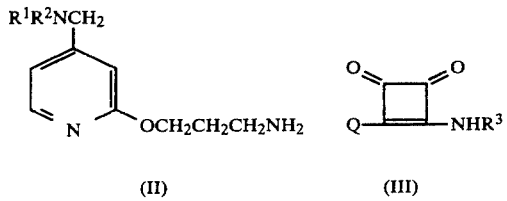

(II)        (III)

wherein $R^1$, $R^2$ and $R^3$ are as defined in relation to formula (I), and Q is a group displaceable by amine; or (b) the reaction of a compound of the formula (IV) with a compound of the formula (V):

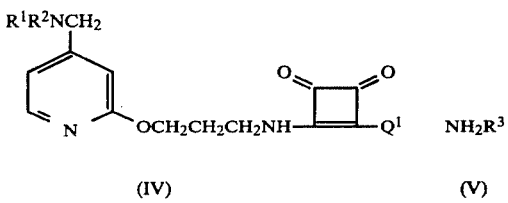

(IV)        (V)

wherein $R^1$, $R^2$ and $R^3$ are as defined in relation to formula (I), and $Q^1$ is a group displaceable by amine; or (c) for compounds of the formula (I) wherein $R^3$ is $C_{1-6}$alkyl, the alkylation of a compound of the formula (I) wherein $R^3$ is hydrogen;

(d) the conversion of a compound of the formula (VI):

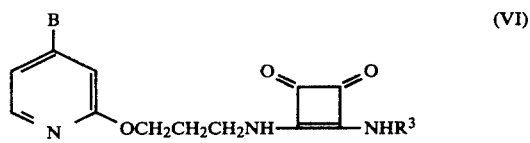

(VI)

wherein B is a precursor of $R^1R^2NCH_2—$, to a compound of the formula (I); or (e) the reaction of a compound of the formula (VII) with a compound of the formula (VIII) or a derivative thereof that permits reaction to occur,

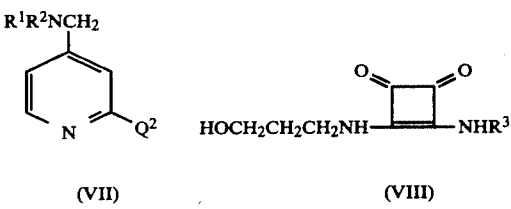

(VII)        (VIII)

wherein $R^1$, $R^2$ and $R^3$ are as defined in relation to formula (I) and $Q^2$ is a group displaceable by hydroxy or its equivalent;

and thereafter if necessary forming a pharmaceutically acceptable acid addition salt.

The compounds of the formula (II) are preparable by the methods of European Patent Application Publication No. 49173. The compounds of the formula (III) are known or may be prepared by the methods of U.S. Pat. No. 4,062,863.

Suitably Q is $C_{1-6}$alkoxy, halo or $C_{1-6}$alkylthio moiety, for example methylthio, methoxy or ethoxy. Of these methoxy is preferred. The reaction may be performed in the absence of solvent or in a solvent for example methanol, ethanol or acetonitrile. In the presence of a solvent the reaction temperature may be for example from ambient to reflux. In the absence of a solvent the reaction temperature is conveniently at an elevated temperature, for example about 120°–160° C.

The compounds of the formula (IV) may be prepared, for example, by the reaction of a compound of the formula (II) with a compound of the formula (IV):

(IX)

wherein $Q^3$ is a better leaving group than $Q^1$, or $Q^3$ and $Q^1$ represent the same moiety, for example methoxy.

The reaction of a compound of the formula (IV) with a compound of the formula (V) is normally carried out in the presence of an excess of the compound of the formula (V). Suitably the reaction is performed in a solvent for example methanol, ethanol, or pyridine. Suitably the reaction temperature may be from ambient to reflux. It may be advantageous to perform the reaction at an elevated pressure. Suitably $Q^1$ is a $C_{1-6}$alkoxy or $C_{1-6}$alkylthio moiety, for example methylthio, methoxy or ethoxy.

The alkylation of the compounds of the formula (I) wherein $R^3$ is hydrogen may be performed in conventional manner, for example via the formation of a Schiff's base and subsequent reduction, or by alkylation with about one mole equivalent of an alkylating agent for example an alkyl halide.

B in the compound of the formula (VI) may include groups such as bromomethyl which may be converted to a group $R^1R^2NCH_2$— in conventional manner. Bromomethyl substituents may be obtained from hydroxymethyl substituents. In an alternative aspect B may be a group —CHO which is reacted with $R^1R^2NH$ under conditions of reductive amination.

Such introduction of the group $R^1R^2NCH_2$— may be performed at any convenient stage of the synthetic procedures outlined herein or in the art.

The compounds of the formula (VI) may be prepared by methods analogous to those of processes (a) to (c) and (e) described herein.

Suitably in the compounds of the formula (VII), $Q^2$ is chloro or bromo. The reaction of a compound of the formula (VII) with a compound of formula (VIII) is generally performed under basic conditions, for example the anion of the compound of the formula (VIII) may be generated, for example using excess sodium hydride in a suitable solvent.

The compounds of the formula (VII) may be prepared by the methods of European Patent Application Publication No. 49173. The compounds of the formula (VIII) may be prepared from a compound of the formula (III) with 3-aminopropanol under conditions analogous to those described above.

Pharmaceutically acceptable acid addition salts of the compounds of the formula (I) may be prepared from the corresponding base of the compounds of the formula (I) in conventional manner. For example the base may be reacted with an acid in a $C_{1-4}$ alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

Suitable pharmaceutically acceptable acid addition salts of the compounds of the formula (I) include those formed with hydrochloride, hydrobromic, sulphuric, phosphoric, acetic, citric, maleic, lactic, ascorbic, fumaric, oxalic, methanesulphonic and ethanesulphonic acids.

During the processes described in this specification any groups may be optionally protected, if appropriate, in conventional manner.

The following Examples serve to illustrate this invention.

EXAMPLE 1

1-[3-[4-(Piperidinomethyl)pyrid-2-yloxy]prop-1-ylamino]-2-aminocyclobut-1-ene-3,4-dione 1-Amino-2-methoxy-cyclobut-1-ene-3,4-dione (0.5 g) and 3-[4-(piperidinomethyl)pyrid-2-yloxy]prop-1-ylamine (1.05 g) were refluxed in ethanol (25 ml) for 4 hours. A solid formed during the reaction. The reaction mixture was cooled and the solid collected by filtration. Recrystallisation of the solid from ethanol/methanol afforded the title product (0.88 g), m.p. 226°–8° C.

EXAMPLE 2

1-[3-[4-(Dimethylaminomethyl)pyrid-2-yloxy]prop-1-ylamino]-2-aminocyclobut-1-ene-3,4-dione 1-Amino-2-methoxy-cyclobut-1-ene-3,4-dione (0.5 g) and 3-[4-(dimethylaminomethyl)pyrid-2-yloxy]prop-1-yl-amine (0.85 g) were refluxed in ethanol in a similar manner to Example 1. The solid obtained was recrystallised from ethanol to give the title product, (0.79 g), m.p. 212°–4° C.

EXAMPLE 3

1-[3-[4-(Dimethylaminomethyl)pyrid-2-yloxy]prop-1-ylamino]-2-aminocyclobut-1-ene-3,4-dione 1-Amino-2-methoxy-cyclobut-1-ene-3,4-dione is mixed with 3-[4-(dimethylaminomethyl)pyrid-2-yloxy]-prop-1-yl-amine in anhydrous pyridine and is heated at reflux temperature to give the title product.

EXAMPLE 4

1-[3-[4-(Piperidinomethyl)pyrid-2-yloxy]prop-1-ylamino]-2-aminocyclobut-1-ene-3,4-dione 1-Amino-2-methoxy-cyclobut-1-ene-3,4-dione is mixed with 3-[4-(piperidinomethyl)pyrid-2-yloxy]prop-1-ylamine in anhydrous pyridine and is heated at reflux temperature to give the title product.

EXAMPLE 5

A pharmaceutical composition for oral administration is prepared comprising:

|  | % (wt/wt) |
| --- | --- |
| the product of Example 1 | 55 |
| dibasic calcium phosphate dihydrate | 20 |
| colouring agent | 0.5 |
| polyvinylpyrrolidone | 4.0 |
| microcrystalline cellulose | 8.0 |
| maize starch | 8.0 |
| sodium glycollate | 4.0 |
| magnesium stearate | 0.5 | by mixing together the product of Example 1, dibasic calcium phosphate dihydrate and colouring agent, adding a concentrated solution of polyvinylpyrrolidone, granulating, drying and screening the dried granules: adding the cellulose, starch, sodium glycollate and magnesium stearate to the granules and compressing into tablets containing 100 mg, 150 mg or 200 mg of the free base of the product of Example 1.

EXAMPLE 6

A pharmaceutical composition for injectable administration is prepared by converting the product of Example 1 into a hydrochloride salt thereof and dissolving this in water for injection (E.P.) to afford a 1–5% (wt/wt) solution. The solution is clarified by filtration and filled into vials which are sealed and sterilised, suitably containing 2 ml of solution.

EXAMPLE 7

1-[3-[4-(Pyrrolidinomethyl)pyrid-2-yloxy]prop-1-ylamino]-2-aminocyclobut-1-ene-3,4-dione By the methods of Example 1, 1-amino-2-methoxycyclobut-1-ene-3,4-dione and 3-[4-(pyrrolidinomethyl)pyrid-2-yloxy]prop-1-ylamine are reacted to form the title product.

EXAMPLE 8

1-[3-[4-(Piperidinomethyl)pyrid-2-yloxy]prop-1-ylamino]-2-(methylamino)cyclobut-1-ene-3,4-dione By the methods of Example 1, 1-(methylamino)-2-methoxycyclobut-1-ene-3,4-dione and 3-[4-(piperidinomethyl)pyrid-2-yloxy]prop-1-ylamine are reacted to form the title product.

DESCRIPTION 1

1-Amino-2-(3-hydroxypropylamino)cyclobut-1-ene-3,4-dione

1-Amino-2-methoxycyclobut-1-ene-3,4-dione (1.27 g) and 3-hydroxypropylamine (0.75 g) were refluxed in ethanol (25 ml) for 4 hours. The reaction mixture was cooled and the solid product collected by filtration. This was washed with ethanol and dried to afford the title compound (1.3 g), m.p. 256°–258° C.; found C 49.27, H 5.88, N 16.38 (calculated C 49.41, H 5.92, N 16.46); δppm 1.69 (2H, m), 3.4–3.7 (4H, m), 4.47 (1H, t, OH), 7.32 (3H, broad, amino protons).

What is claimed is:

1. A compound of the formula (I):

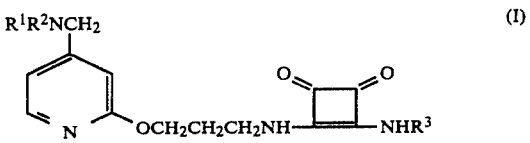

or a pharmaceutically acceptable salt thereof, wherein
$R^1$ and $R^2$ are independently hydrogen or $C_{1-6}$ alkyl, or $R^1R^2N$ represents 2,2,2,-trifluoroethylamino; or $R^1$ and $R^2$ form a $-(CH_2)_n-$ linkage, wherein n is 4–6, so that together with the nitrogen atom to which they are attached they form a 5–7 membered ring; and
$R^3$ is hydrogen or $C_{1-6}$ alkyl.

2. A compound according to claim 1 wherein $R^1R^2N-$ is dimethylamino.

3. A compound according to claim 1 wherein $R^1R^2N-$ is piperidino.

4. A compound according to any one of claims 1 to 3 wherein $R^3$ is hydrogen.

5. A compound according to claim 1 which is 1-[3-[4-(piperidinomethyl)pyrid-2-yloxy]prop-1-ylamino]-2-aminocyclobut-1-ene-3,4-dione or a pharmaceutically acceptable salt thereof.

6. A compound according to claim 1 which is 1-[3-[4-(dimethylaminomethyl)pyrid-2-yloxy]prop-1-ylamino]-2-aminocyclobut-1-ene-3,4-dione or a pharmaceutically acceptable salt thereof.

7. A pharmaceutical composition haaving histamine $H_2$-receptors antagonist activity which comprises an effective amount to block said receptors of a compound of claim 1 together with a pharmaceutically acceptable carrier.

8. A method of blocking histamine $H_2$-receptors which comprises administering to an animal an effective amount to block said receptors of a compound of claim 1.

* * * * *